US006758886B2

(12) United States Patent
Vellinga

(10) Patent No.: US 6,758,886 B2
(45) Date of Patent: Jul. 6, 2004

(54) THREE-PHASE SEPARATOR AND INSTALLATION FOR BIOLOGICAL PURIFICATION OF EFFLUENT

(75) Inventor: Sjoerd Hubertus Jozef Vellinga, Tjalleberd (NL)

(73) Assignee: Paques Water Systems, B.V., Balk (NL)

( * ) Notice: Subject to any disclaimer, the term of this patent is extended or adjusted under 35 U.S.C. 154(b) by 0 days.

(21) Appl. No.: 10/234,380

(22) Filed: Sep. 5, 2002

(65) Prior Publication Data

US 2003/0046912 A1 Mar. 13, 2003

(30) Foreign Application Priority Data

Sep. 7, 2001 (NL) .............................................. 1018909

(51) Int. Cl.⁷ .............................................. B01D 19/00
(52) U.S. Cl. ............................. 96/184; 95/253; 95/254; 95/260; 95/262; 96/204; 96/206; 96/220; 210/538; 210/539; 210/801; 210/804
(58) Field of Search ........................ 96/184, 204, 206, 96/220; 95/253, 254, 259–262; 210/538, 539, 801, 804

(56) References Cited

U.S. PATENT DOCUMENTS

| 3,009,537 A | * 11/1961 | Glasgow et al. ............... 96/159 |
| 3,347,773 A | * 10/1967 | Turner ......................... 204/662 |
| 3,389,536 A | *  6/1968 | Bull ............................. 96/184 |
| 4,012,207 A | *  3/1977 | Jones ........................... 96/184 |
| 4,059,517 A | * 11/1977 | Strahorn et al. .............. 95/253 |
| 4,165,285 A | 8/1979 | Wind et al. ............... 210/195.3 |
| 4,210,176 A | * 7/1980 | Emming ...................... 137/573 |
| 4,253,956 A | 3/1981 | Pette .......................... 210/188 |
| 4,604,196 A | * 8/1986 | Lowrie et al. ................ 96/176 |
| 4,995,495 A | * 2/1991 | Krynski ....................... 196/46 |
| 5,904,850 A | * 5/1999 | Vellinga ..................... 210/603 |
| 6,063,273 A | * 5/2000 | Habets et al. ............... 210/188 |

FOREIGN PATENT DOCUMENTS

| EP | 244029 | * 11/1987 |
| EP | 949463 | * 10/1999 |
| FR | 722 935 | 3/1932 |
| JP | 58-170509 | * 10/1983 ................. 95/262 |

OTHER PUBLICATIONS

*References X'd were cited by applicant on p. 1 of the specification.*

* cited by examiner

Primary Examiner—Richard L. Chiesa
(74) Attorney, Agent, or Firm—Young & Thompson

(57) ABSTRACT

A three-phase separator for separating off from a fluid gas and particles contained therein, includes at least one pair of two gas collection caps extending in a horizontal longitudinal direction (L) and each having a plate section. The plate sections converge in the downward direction. At the bottom ends the plate sections leave an inlet passage, elongated in the longitudinal direction, for the fluid containing particles and an outlet passage, elongated in the longitudinal direction, for settled particles. A discharge opening for fluid, opening into the settling chamber, is provided at a level higher than the inlet and outlet passages. The inlet passage and the outlet passage are located in the extension of one another, viewed in the longitudinal direction.

15 Claims, 3 Drawing Sheets

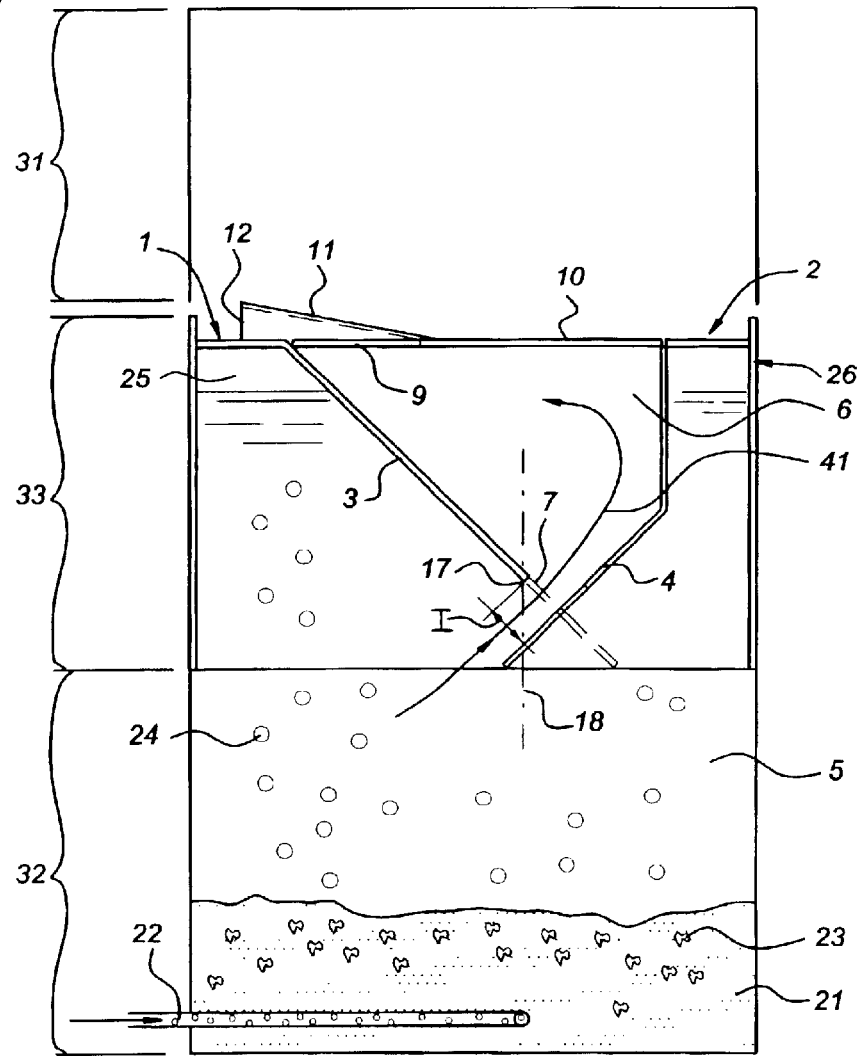
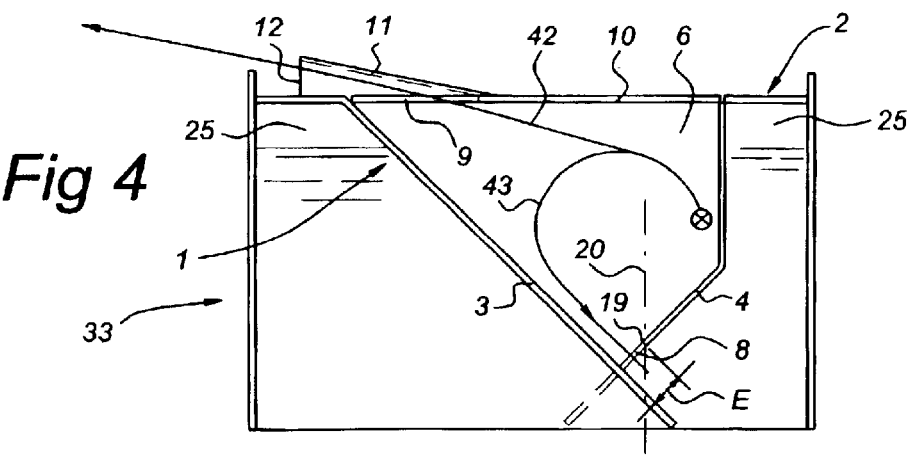

THREE-PHASE SEPARATOR AND INSTALLATION FOR BIOLOGICAL PURIFICATION OF EFFLUENT

FIELD OF THE INVENTION

The present invention relates to a three-phase separator for separating off from a fluid gas and particles contained therein, comprising at least one pair of two gas collection caps extending in a horizontal longitudinal direction and each having a plate section, wherein the plate sections converge in the downwards direction and at the bottom ends of the plate sections leave at least one passage, elongated in the longitudinal direction, for the fluid and particles, which passage connects a reactor chamber below the plate sections to a settling chamber above the plate sections, and wherein a discharge opening for fluid, opening into the settling chamber, is provided at a level higher than said at least one passage.

BACKGROUND OF THE INVENTION

A three-phase separator of this type is generally known. Inter alia, EP-A 244 029 and EP-A 949 463 may be mentioned. Three-phase separators of this type are widely used in installations for the biological purification of water. Such installations comprise a reactor in which a layer of bacterial flocs is provided. Feed means for the water to be purified open into the layer of bacterial floes and above the layer of bacterial flocs means are provided for allowing particles to settle, in particular bacterial flocs, and discharging purified water. The principle according to which such known installations operate is that effluent is fed into a reactor from the bottom and that this water streams upwards through a layer of bacterial floes, dissolved organic pollutants which come into contact with the bacteria being converted into methane and carbon dioxide. The gas produced in this way gives rise to turbulence, as a result of which bacterial floes swirl upwards. The liberated gas is collected below the gas caps of the three-phase separator in order then to be discharged. Settling of the bacterial floes initially entrained by the gas then takes place above the gas caps. These bacterial floes then fall back into the reactor chamber and purified water remains above the cap, which water is discharged.

When the fluid and bacterial floes pass between the gas collection caps a certain acceleration of the fluid takes place, as a result of which it becomes difficult, if not impossible, for the bacterial floes to settle back into the reactor chamber against that flow. In order to counteract this, the gas caps are usually positioned as far apart as possible; after all, a large gap reduces the said fluid acceleration. The disadvantage of placing the gas caps as far apart as possible is, in turn, that the gas bubbles are then also able to escape between the gas caps, which again causes the fluid velocity to increase and, moreover, also leads to inadequate capture of gas bubbles. In order to counteract this, several layers of gas caps are installed, the gas caps in an upper layer overlapping the gap between gas caps in a layer below. The various aspects result in constructions that contain a relatively large number of components and take up a relatively large amount of space.

SUMMARY OF THE INVENTION

The aim of the present invention is to provide an improved three-phase separator, which is of a simplified construction and which can be implemented with relatively little structural material.

The abovementioned aim is achieved with a three-phase separator of the type indicated in the preamble, in that said at least one passage comprises an inlet passage for the fluid containing the particles to be separated off, as well as an outlet passage for particles which have settled in the settling chamber;

in that the inlet passage and the outlet passage are in the extension of one another, viewed in the longitudinal direction; and in that the discharge opening, viewed in the longitudinal direction and from the inlet passage, is provided level with the outlet passage or beyond the outlet passage.

In the case of the three-phase separator according to the invention the fluid stream containing particles is forced to move horizontally after passage between two gas collection caps, in particular passage between the plate sections thereof. The reason for this horizontal movement is that the discharge opening has been displaced in the horizontal direction, i.e. the longitudinal direction, with respect to the inlet passage. During this movement the fluid velocity decreases as a consequence of the space through which the fluid has to flow, i.e. the settling chamber, becoming wider. As a consequence of the lower fluid velocity, the bacterial flocs settle and, after some horizontal displacement, pass through the outlet passage back into the reactor chamber located below the caps.

According to the invention it is advantageous if the surface area of the inlet passage is greater than the surface area of the outlet passage. When the surface area of the inlet passage is chosen to be greater than the surface area of the outlet passage, the inlet passage will offer lower resistance than the outlet passage to the upward fluid stream, as a consequence of which the rising fluid stream will automatically select the inlet passage as inlet, so that the outlet passage is able to allow the settled sludge to fall back into the reactor chamber via the outlet passage of smaller surface area.

According to an advantageous embodiment of the invention the surface area of the inlet passage is at least 30%, preferably at least 60%, such as, for example, approximately 70%, greater than the surface area of the outlet passage. It has been found that with a difference of approximately 25% in the magnitude of the surface area although the three-phase separator does not function in the optimum manner it does function reasonably and that the separation capacity with regard to the entrained particles is good from a difference in width of 50% and that, in particular, very good results can be achieved with a difference in width of approximately 70%.

In order further to minimize the risk of incorrect fluid flow through the outlet passage, it is preferable according to the invention if the surface area of the inlet passage is at most 5×, preferably at most 3×, as large as the surface area of the outlet passage. In this way it is ensured that the outlet passage is sufficiently large to allow passage of the stream of separated particles, often also with some fluid as well in which the particles, as it were, can still float.

According to a further advantageous embodiment of the invention, viewed with respect to a first vertical touching a first bottom edge part of the one plate section, at the location of the inlet passage, the other plate section extends underneath said first bottom edge part to beyond said first vertical. In this way the underside of the inlet passage is screened by a continued projecting part of a plate section, so that rising gas bubbles are prevented from passing through the inlet passage, or at least it is made more difficult for them to do so. For the same reason it is advantageous if, viewed with respect to a second vertical touching a second bottom edge part of the other plate section, at the location of the outlet passage, the one plate section extends underneath said second bottom edge part to beyond said second vertical. The screening of the outlet passage by means of a section of a plate section continued beneath it, in combination with the screening of the inlet passage from the underside by means of a section of the other plate section continued beneath it, has the advantage that what is achieved at the same time is that the inlet passage and the outlet passage open in different directions (with respect to a vertical) and that it is thus made more difficult for particles flowing back into the reactor chamber via the outlet passage to be immediately entrained again so as to return to the settling chamber through the inlet passage.

According to a further advantageous embodiment of the invention, the settling chamber is provided with a ceiling that closes off this settling chamber from above and that at the longitudinal edges on either side adjoins the respective caps and the discharge opening is provided in the ceiling and, preferably, the top of the discharge opening is covered by a discharge cap with an outflow opening opening in the horizontal direction. This embodiment is particularly advantageous when an aerobic reactor is placed on top of an anaerobic reactor, which aerobic and anaerobic reactors are then separated from one another by the three-phase separator.

According to a further aspect, the present invention relates to an installation for biological purification of effluent, comprising a three-phase separator according to the invention, wherein a layer of particles in the form of bacterial floes, such as sludge or granules, is present in the bottom of the reactor chamber and wherein a feed for the effluent to be purified opens into or below said layer. With the installation according to the invention it is particularly advantageous if the discharge opening is in communication with a further reactor chamber of, in particular, a biological reactor.

BRIEF DESCRIPTION OF THE DRAWINGS

The present invention will be explained in more detail below with reference to an illustrative embodiment shown in the drawing. In the drawing:

FIG. 3 shows a section along the arrows III in FIG. 1 with a top reactor above it and a bottom reactor below it, which reactors are also indicated diagrammatically;

FIG. 4 shows a section along the arrows IV in FIG. 1;

DETAILED DESCRIPTION OF THE INVENTION

Figure 5:
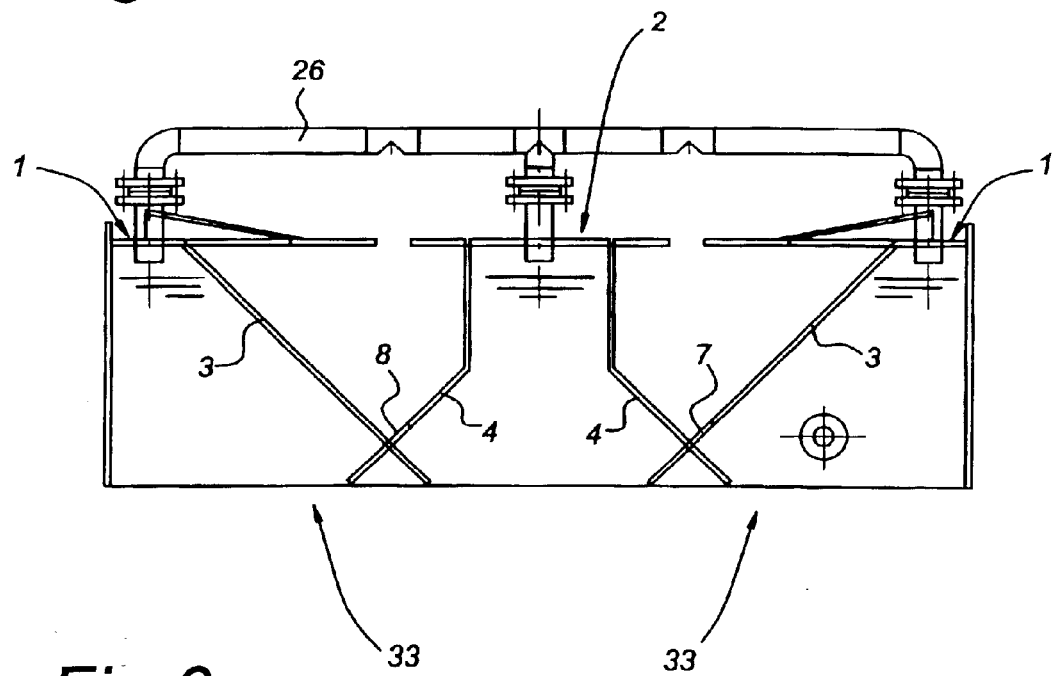
FIG. 5 shows, diagrammatically, a sectional view of a dual three-phase separator according to the invention.

The figures show a three-phase separator 33, FIG. 5 then showing a dual three-phase separator 33. The three-phase separator according to the invention consists of a pair of two gas collection caps 1 and 2, each having a plate section 3 and 4, respectively. These plate sections 3 and 4 converge in a downward direction and leave two elongated passages 7, 8 at their bottom ends, The one elongated passage is an inlet passage 7 and the other passage is an outlet passage 8. The inlet passage 7 and the outlet passage 8 are located in the extension of one another viewed in the longitudinal direction L. Viewed transversely to the longitudinal direction L, the width I of the inlet passage 7 is greater than the width E of the outlet passage 8. The width I of the inlet passage 7 is, for example, 90 mm, whilst the width E of the outlet passage 8 is 70 mm. More particularly, the range of the width of the two passages will be between 40 and 120 mm.

A reactor chamber 5 is located below the caps 1 and 2 and a settling chamber 6 is located above the caps 1 and 2, or at least between the caps 1 and 2. A discharge opening 9 opens into the settling chamber 6 level with the outlet passage 8, viewed in the longitudinal direction L, which discharge opening 9 in the example is made in a ceiling/lid 10, the two longitudinal sides of which adjoin, on either side, the caps 1 and 2 so as, together with end partitions 36, to close off the settling chamber 6 all round except for the inlet passage, the outlet passage and the discharge opening. The top of the discharge opening 9 is covered by a cap 11 having an outflow opening 12 opening in the horizontal direction.

With reference, in particular, to FIG. 3 and viewed with respect to the first vertical 18, the plate section 4 extends underneath to beyond the bottom edge 17 of the plate section 3 so as completely to overlap the inlet passage 7, viewed in the vertical direction.

With reference to, in particular FIG. 4, the plate section 3 extends, with respect to a second vertical 20, which touches the bottom edge 19 of the plate section 4, underneath and beyond said bottom edge 19 of said plate section 4 so as completely to overlap the outlet passage 8, viewed in the vertical direction.

Viewed in the longitudinal direction L, in the example shown the length of the inlet passage 7 is, for example, 850 mm and the length of the outlet passage 8 is, for example, 650 mm.

With reference to FIG. 3, and also to FIGS. 1, 2 and 4, the mode of operation of the three-phase separator 33 according to the invention can be described as follows:

The reactor chamber 5 forms part of a bottom reactor 32. This bottom reactor 32 is, in particular, a UASB (Upflow Anaerobic Sludge Blanket) reactor. In such a reactor there is a layer 21 of bacterial floes, which can be either in sludge form or in granular form, at the bottom. Effluent to be purified is fed into this layer 21 in the reactor via a water feed 22. This water that is fed in streams upwards through the layer 21, dissolved organic pollutants, which come into contact with the bacteria, being converted into methane and carbon dioxide. The gas thus produced gives rise to turbulence, as a result of which particles from the layer 21, in particular bacterial floes, swirl upwards. The gas bubbles 24 are captured at the top of the gas caps 1 and 2, where a gas chamber 25 forms, from which the gas is discharged via the gas discharge 26. The rising volume stream, still containing particles, will enter the settling chamber 6 between the plate sections 3 and 4 so as to allow the particles to settle in the settling chamber 6, after which so-called clarified water remains, which is discharged via the passage 9.

The stream of fluid and particles in the three-phase separator 33 is indicated in its entirety by a curved arrow 40. The arrow 40 is subdivided into the section 41, the section 42 and the branch 43. Considered in more detail, see in particular FIG. 3, the fluid stream containing entrained particles tends to enter the settling chamber 6 via the inlet passage 7; see arrow section 41 in FIG. 3. The rising volume stream has a preference for the inlet passage 7 over the outlet passage 8 as a consequence of the greater width I of the inlet passage 7 than that, E, of the outlet passage 8. Because, viewed in the longitudinal direction L, the discharge passage is some distance away from the inlet passage 7, the volume stream that has entered the settling chamber 6 is forced to move horizontally, whilst, at the same time, following the arrow 41 in the direction of the arrow, the settling chamber 6 becomes wider, as a consequence of which the particles can start to settle on, in particular, plate section 3 and possibly also plate section 4, so as, as is indicated by branch arrow 43, to be able to fall back into the reactor chamber 5 via the outlet passage 8. The clarified volume stream of fluid will then, as is indicated by arrow section 42 in FIG. 4, leave the settling chamber 6 via outlet passage 9. As will be clear from the above, the volume stream describes a sort of horizontally extending corkscrew movement in the settling chamber 6.

The settling chamber 6 from the ceiling plate 10 covering the top is not necessary per se. It is, for example, also conceivable that one or more outlet passages in the form of overflow passages or overflow edges are provided in the rear end partition 36 located some distance away from the inlet passage in FIG. 2, via which overflow passages or overflow edges completely or partially clarified fluid would be able to leave the settling chamber 6. However, the passage, covered by a cap 11, in a ceiling plate 10 closing off the settling chamber 6 from above has the advantage that yet a further reactor can be placed on top of the three-phase separator 33. This further reactor can be, for example, an anaerobic reactor, just like the bottom reactor 32, but the top reactor 31 can also be an aerobic reactor whilst the bottom reactor 32 is an anaerobic reactor. The reason for this is that the ceiling plate 10 and the passage 9 covered from above by a cap 11 preclude undesirable fluid communication from the top, aerobic reactor 31 via the three-phase separator 33 to the bottom anaerobic reactor 32.

However, it will also be clear that the bottom reactor 32 can very well be an aerobic reactor, in which case air or oxygen is then separated off from the fluid in the three-phase separator 33.

FIG. 5 shows a dual three-phase separator 33 according to the invention. This dual three-phase separator 33 has, as it were, a common gas cap 2 with each separator having its own plate section 4, the plate sections 4 diverging towards the bottom. In the case of a dual embodiment of this type, the options will be to allow either the inlet passages or the outlet passages to open towards one another, viewed transversely to the longitudinal direction L, that is to say viewed transversely to the plane of the drawing in FIG. 5. In the example shown in FIG. 5 the option chosen is to allow the outlet passages 8 to open towards one another, that is to say to allow both to open under the common cap 2. Furthermore, it will be clear that the inlet passage 7 of the one three-phase separator completely overlaps the outlet passage 8 of the other three-phase separator and that, because the length (viewed perpendicularly to the plane of the drawing in FIG. 5) of the inlet passage 7 is always preferably greater than that of the outlet passage 8, the inlet passage 7 of the one three-phase separator also partially overlaps the inlet passage 7 of the other three-phase separator.

Figure 1:
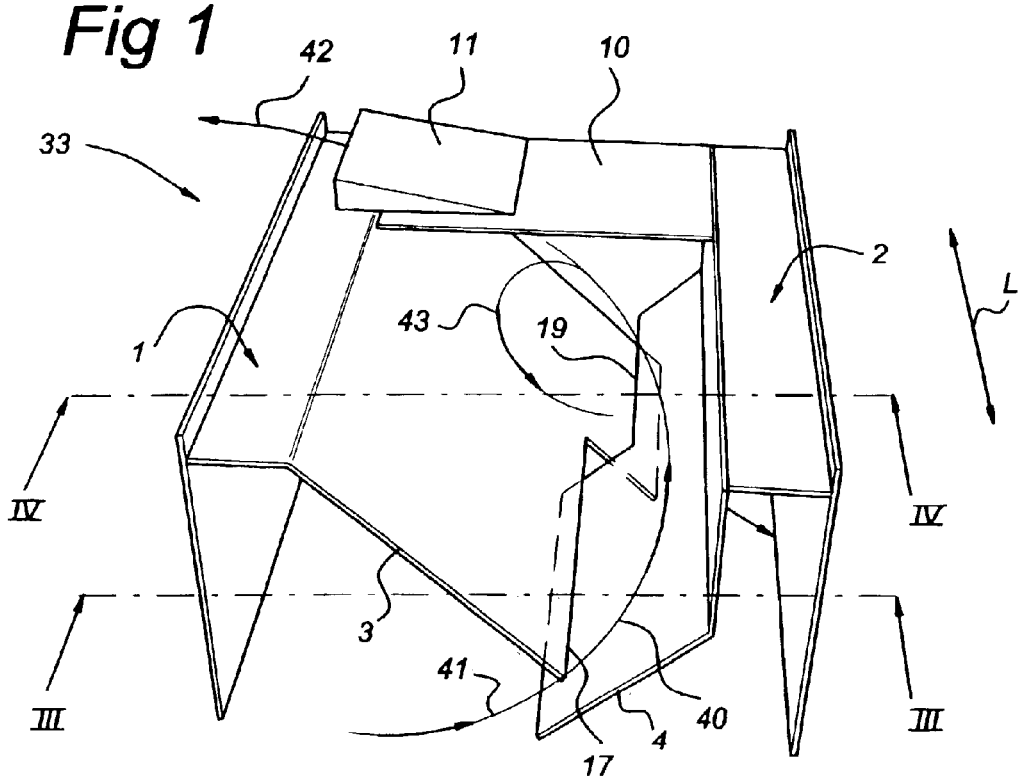
FIG. 1 shows a perspective view of a three-phase separator according to the invention in an exploded view, or at least shown in an exploded view.
Figure 2:
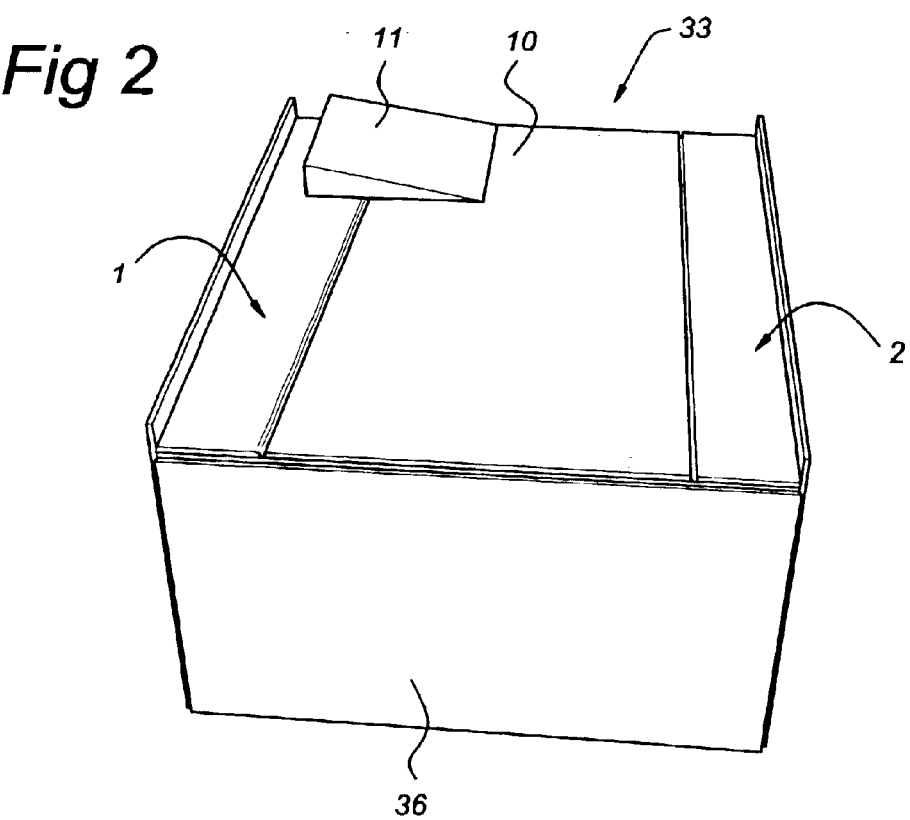
FIG. 2 shows a perspective view of the three-phase separator according to the invention shown in exploded view in FIG. 1.
Figure 6:
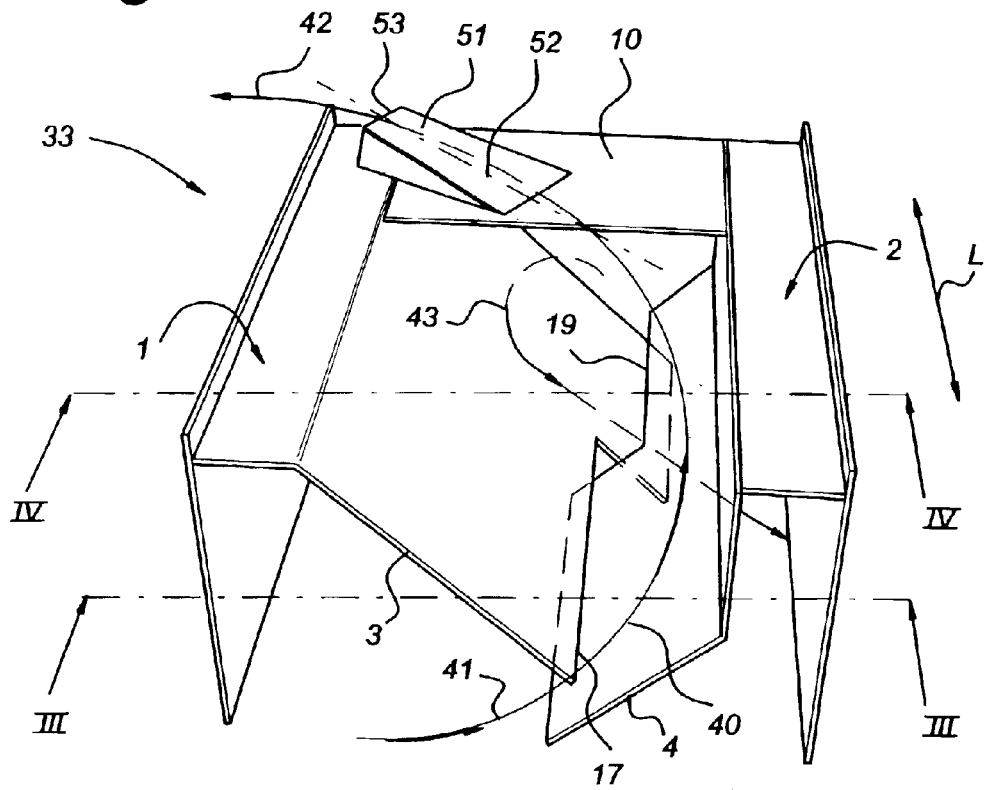
FIG. 6 shows, as a variant of FIG. 1, an example of a further three-phase separator according to the invention.

FIG. 6 shows, as a variant of FIG. 1, a further three-phase separator according to the invention. Insofar as FIGS. 1 and 6 do not differ, the same reference numerals have been used. There are two differences between FIGS. 1 and 6. The first difference is that the discharge cap 51 in FIG. 6 has a different orientation to the discharge cap 11 in FIG. 1. The outflow opening 53 has been turned more in the direction of the corkscrew-like movement 40, in particular section 42 thereof. In other words, the axis 52 is at an angle of less than 90°, such as approximately 45°, with respect to the longitudinal direction L. The second difference, which is to be regarded separately from the first difference, lies in the shape of the cap 51. The top surface of the outflow cap 52 is constructed such that it narrows, in particular tapers, in the outflow direction.

What is claimed is:

1. Three-phase separator for separating off from a fluid gas and particles contained therein, comprising at least one pair of two gas collection caps extending in a horizontal longitudinal direction and each having a plate section, wherein the plate sections converge in the downwards direction and at the bottom ends of the plate sections leave at least one passage, elongated in the longitudinal direction, for the fluid and particles, which passage connects a reactor chamber below the plate sections to a settling chamber above the plate sections and wherein a discharge opening for fluid, opening into the settling chamber, is provided at a level higher than said at least one passage;

wherein said at least one passage comprises an inlet passage for the fluid containing the particles to be separated off, as well as an outlet passage for particles which have settled in the settling chamber;

the inlet passage and the outlet passage are in extension of one another, viewed in the longitudinal direction; and the discharge opening, viewed in the longitudinal direction and from the inlet passage, is provided level with the outlet passage or beyond the outlet passage.

2. Three-phase separator according to claim 1, wherein the surface area of the inlet passage is greater than the surface area of the outlet passage.

3. Three-phase separator according to claim 1, wherein the surface area of the inlet passage is at least 30% greater than the surface area of the outlet passage.

4. Three-phase separator according to claim 1, wherein the surface area of the inlet passage is at least 60% greater than the surface area of the outlet passage.

5. Three-phase separator according to claim 1, wherein the surface area of the inlet passage is at most 5 times as large as the surface area of the outlet passage.

6. Three-phase separator according to claim 1, wherein the surface area of the inlet passage is at most 3 times as large as the surface area of the outlet passage.

7. Three-phase separator according to claim 1, wherein, viewed with respect to a first vertical touching a first bottom edge part of the one plate section, at the location of the inlet passage, the other plate section extends underneath said first bottom edge part to beyond said first vertical.

8. Three-phase separator according to claim 7, wherein, viewed with respect to a second vertical section touching a second bottom edge part of the other plate section, at the location of the outlet passage, the one plate section extends underneath said second bottom edge part to beyond said second vertical.

9. Three-phase separator according to claim 1, wherein the settling chamber is provided with a ceiling that closes off the settling chamber from above and at the longitudinal edges on either side adjoins the respective caps and the discharge opening is provided in the ceiling.

10. Three-phase separator according to claim 9, wherein the top of the discharge opening is covered by a discharge cap with an outflow opening which opens in the horizontal direction.

11. Installation for biological purification of effluent, comprising a three-phase separator according to claim 9, wherein a layer of particles in the form of bacterial flocs is present in the bottom of the reactor chamber and wherein a feed for the effluent to be purified opens into or below said layer.

12. Installation according to claim 11, wherein the discharge opening is in communication with a further reactor chamber.

13. Installation according to claim 12, wherein the further reactor chamber comprises a biological reactor.

14. Installation for biological purification of effluent, comprising a three-phase separator according to claim 1, wherein a layer of particles in the form of bacterial flocs is present in the bottom of the reactor chamber and wherein a feed for the effluent to be purified opens into or below said layer.

15. Three-phase separator according to claim 1, wherein, viewed with respect to a second vertical touching a second bottom edge part of the other plate section, at the location of the outlet passage, the one plate section extends underneath said second bottom edge part to beyond said second vertical.

* * * * *